United States Patent
Zierhofer

(10) Patent No.: US 7,283,876 B2
(45) Date of Patent: Oct. 16, 2007

(54) ELECTRICAL STIMULATION OF THE ACOUSTIC NERVE BASED ON SELECTED GROUPS

(75) Inventor: Clemens M. Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 175 days.

(21) Appl. No.: 11/076,446

(22) Filed: Mar. 8, 2005

(65) Prior Publication Data
US 2005/0203589 A1 Sep. 15, 2005

Related U.S. Application Data

(60) Provisional application No. 60/551,318, filed on Mar. 8, 2004.

(51) Int. Cl.
*A61N 1/00* (2006.01)
*A61B 5/04* (2006.01)

(52) U.S. Cl. .................. 607/57; 607/137; 600/379
(58) Field of Classification Search ........... 607/55–57, 607/137; 600/379
See application file for complete search history.

(56) References Cited

U.S. PATENT DOCUMENTS

| | | | |
|---|---|---|---|
| 4,515,158 A | 5/1985 | Patrick et al. | 128/419 R |
| 5,151,158 A | 9/1992 | Bowen et al. | 128/419 R |
| 6,778,858 B1* | 8/2004 | Peeters | 607/57 |
| 2001/0031909 A1 | 10/2001 | Faltys et al. | 600/25 |
| 2004/0082985 A1 | 4/2004 | Faltys et al. | 607/116 |

FOREIGN PATENT DOCUMENTS

| WO | WO99/49815 | 10/1999 |
|---|---|---|
| WO | WO 01/19304 A1 | 3/2001 |

OTHER PUBLICATIONS

International Search Report dated Nov. 16, 2005.

* cited by examiner

*Primary Examiner*—Carl Layno
*Assistant Examiner*—Natasha Patel
(74) *Attorney, Agent, or Firm*—Bromberg & Sunstein LLP

(57) ABSTRACT

In accordance with one embodiment of the invention, a method of activating electrodes in a multichannel electrode array is provided. Each channel is associated with a different electrode in the array. At least two groups of channels in the multichannel electrode array are selected, wherein at least one of the selected groups includes a plurality of channels. One or more channels in each selected group is selected, and the electrodes associated with each selected channel are activated. The steps of selecting at least one channel in each selected group, and activating the electrodes associated with each selected channel are repeated, such that the selected channels in at least one selected group varies.

22 Claims, 3 Drawing Sheets

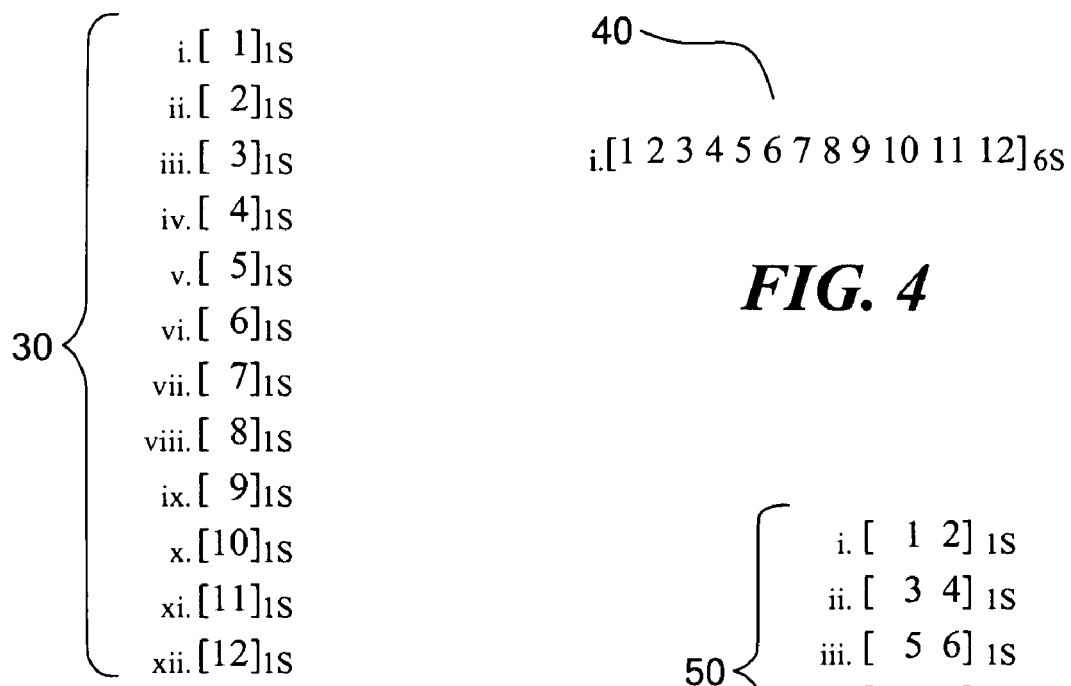
*FIG. 3*
*FIG. 4*
*FIG. 5*
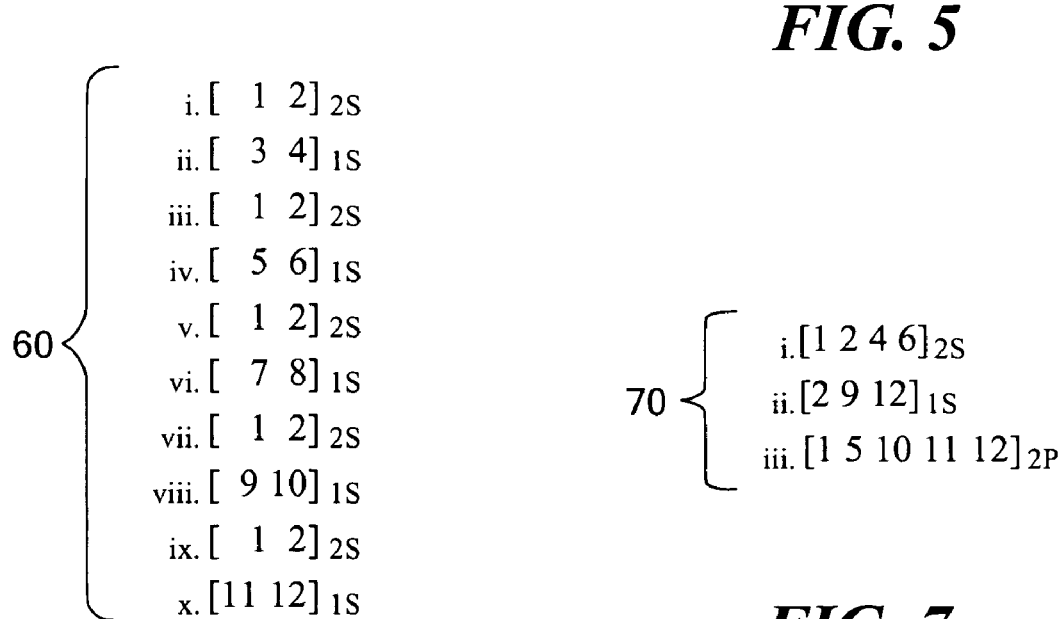
*FIG. 6*
*FIG. 7*

ELECTRICAL STIMULATION OF THE ACOUSTIC NERVE BASED ON SELECTED GROUPS

CROSS REFERENCE TO RELATED APPLICATIONS

This application claims priority from U.S. provisional patent application Ser. No. 60/551,318 filed Mar. 8, 2004, entitled "Electrical Stimulation of the Acoustic Nerve Based on Selected Groups," which is hereby incorporated herein by reference, in its entirety.

TECHNICAL FIELD

The present invention relates to electrical nerve stimulation, and more particularly, electrostimulation of the nerve based on a "selected group" stimulation strategy.

BACKGROUND ART

Cochlear implants (inner ear prostheses) are an option for helping profoundly deaf or severely hearing impaired persons. Unlike conventional hearing aids, which just apply an amplified and modified sound signal, a cochlear implant is based on direct electrical stimulation of the acoustic nerve. The intention of a cochlear implant is to stimulate nervous structures in the inner ear electrically in such a way that hearing impressions most similar to normal hearing are obtained.

FIG. 1 shows a conventional cochlear prosthesis. The cochlear prosthesis essentially consists of two parts, the speech processor 101 that is typically positioned externally proximate the ear, and the implanted stimulator 105. The speech processor 101 typcially includes the power supply (batteries) of the overall system and is used to perform signal processing of the acoustic signal to extract the stimulation parameters. The stimulator 105 generates the stimulation patterns and conducts them to the nervous tissue by means of an electrode array 107 that extends into the scala tympani 109 in the inner ear. The connection between the speech processor 101 and the stimulator 105 is established either by means of a radio frequency link (transcutaneous) using primary coils' 103 and secondary coils within stimulator 105, or by means of a plug in the skin (percutaneous).

One basic problem in cochlear implant applications is spatial channel interaction. Spatial channel interaction means that there is considerable geometric overlapping of electrical fields at the location of the excitable nervous tissue, if different stimulation electrodes (positioned in the scala tympani) are activated. Thus the same neurons are activated if different electrodes are stimulated. Spatial channel interaction is primarily due to the conductive fluids and tissues surrounding the stimulation electrode array.

At present, the most successful stimulation strategy is the so called "continuous-interleaved-sampling strategy" (CIS) introduced by Wilson B S, Finley C C, Lawson D T, Wolford R D, Eddington D K, Rabinowitz W M, "Better Speech Recognition with Cochlear Implants," Nature, vol. 352, 236-238, July 1991, which is incorporated herein by reference.

Signal processing for CIS in the speech processor typically involves the following steps:

(1) splitting up of the audio frequency range into spectral bands by means of a filter bank;

(2) envelope detection of each filter output signal; and (3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals (step (3) above). These signals are sampled sequentially, and the stimulation pulses are applied in a strictly non-overlapping sequence. Thus, the problem of spatial channel interaction is defused and a comparatively precise definition of electrical fields in the cochlea is achieved.

For example, consider a 12-channel CIS-system with a maximum overall stimulation rate of 18 kpps. Assuming that each channel is addressed once in a cycle, the stimulation rate per channel is 1.5 kpps. Such a stimulation rate per channel usually is sufficient for adequate temporal representation of the envelope signal.

The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 μs, which approaches the lower limit.

A stimulation strategy closely related to CIS is the so-called "N-of-M" strategy, wherein only the N electrode channels with maximum energy are selected out of the total number of M channels during each stimulation cycle, as described by Wilson B S, Finley C C, Farmer J C, Lawson D T, Weber B A, Wolford R D, Kenan P D, White M W, Merzenich M M, Schindler R A, "Comparative studies of speech processing strategies for cochlear implants," Laryngoscope 1998; 98:1069-1077, which is incorporated herein by reference. Typically, number M is constant and equal to the overall number of usable channels. Thereby the instantaneous stimulation rate of a selected channel is increased by a factor of M/N. Interestingly, N-of-M strategies do not seem not to improve speech perception as compared to standard CIS, as described in Ziese M, Stützel A, von Specht H, Begali K, Freigang B, Sroka S, Nopp P, "Speech understanding with CIS and N-of-M Strategy in the MED-EL COMBI 40+ system," ORL 2000; 62:321-329, which is incorporated herein by reference.

One disadvantage of N-of-M strategies (with constant M) is that neurons or ensembles of neurons may suffer "microshocks", if electrode channels are switched from "inactive" to "active". For example, consider a situation where a train of supra-threshold pulses is switched on at a particular electrode. The initial pulse in the train will cause action potentials in the majority of neurons that are close to the electrode, followed by a refractory period in which a more limited neural response can be elicited. The majority of the neurons will continue to be at similar refractory states, until sufficient time has passed to cause a sufficient distribution of refractory states. Thus, for at least an initial period of time, the majority of neurons will respond in the same manner to each pulse due to their similar refractory state, as described by Wilson B S, Finley C C, Farmer J C, Lawson D T, Zerbi M, "Temporal representation with cochlear implants," Am. J. Otology, Vol. 18, No. 6(Suppl), S30-S34, 1997, which is incorporated herein by reference.

In standard CIS, periods with no activity at particular electrodes do not occur, since each electrode is stimulated in each cycle, and minimum pulse amplitudes are usually close to or slightly above thresholds. So even when there is no spectral energy present in a particular frequency band, the associated electrode will be active, keeping neurons in different refractory states. Additionally, a number of neurons may be kept busy because of activity of neighboring channels. In this respect, spatial channel interaction can have an (unintentional) advantageous effect.

SUMMARY OF THE INVENTION

In accordance with one aspect the invention, a method of activating electrodes in a multichannel electrode array is provided. Each channel is associated with a different electrode in the array. At least two groups of channels in the multichannel electrode array are selected, wherein at least one of the selected groups includes a plurality of channels. One or more channels in each selected group is selected. The electrodes associated with each selected channel are then activated. The steps of selecting one or more channels in each selected group, and activating the electrodes associated with each selected channel are repeated, such that the selected channels in at least one selected group varies. Compared to standard CIS, the above-described method can be used to increase the instantaneous stimulation rate of a selected channel. Additionally, the above-described method may advantageously be implemented in a manner that ensures continuous activity in all cochlear regions, unlike conventional N-of-M strategies.

In related embodiments of the invention, the electrodes associated with each selected channel may be activated simultaneously or sequentially. Activating the electrodes associated with each selected channel may include applying compensation for channel interaction. The steps of selecting one or more channels in each selected group and activating the electrodes associated with each selected channel may be cyclically repeated. The multichannel electrode array may be part of a cochlear implant, the method further including positioning the multichannel electrode array so as to stimulate the acoustic nerve.

In further related embodiments, selecting the at least two groups of channels includes selecting a first group of channels that includes neighboring electrodes. Due to spatial channel interaction, activating one of the neighboring electrodes in the first group provides stimulation to those regions of the acoustic nerve associated with all of the neighboring electrodes in the first group.

Each channel may be associated with a different filter in a filter bank, wherein the method further includes applying an acoustic representative electrical signal to the bank of filters, and wherein activating the electrodes of each selected channel includes performing at least one of envelope detection and nonlinear compression on the selected channel's filter output. Selecting the one or more channels in each selected group may be based, at least in part, on a comparison of the filter outputs associated with the channels in the selected group.

In accordance with another aspect of the invention, a system for stimulating electrodes is presented. The system includes a multichannel electrode array, each channel associated with a different electrode in the array. A controller defines at least two groups of channels in the multichannel array such that at least one of the defined groups includes a plurality of channels. The controller selects one or more channels in each group, and the electrodes associated with each selected channel are activated. The controller repeats selecting one or more channels in each selected group, and activating the electrodes associated with each selected channel, such that the selected channels in at least one selected group varies.

In related embodiments of the invention, the controller may activate the electrodes associated with each selected channel in a simultaneous or sequential manner. The controller may apply compensation for channel interaction. The controller may cyclically repeat selecting at least one channel in each selected group and activating the electrodes associated with each selected channel. The multichannel electrode array may be part of a cochlear implant for simulating the acoustic nerve. The controller may define a first group of channels that includes neighboring electrodes, wherein, due to spatial channel interaction, activating one of the neighboring electrodes in the first group provides stimulation to those regions of the acoustic nerve associated with all of the neighboring electrodes in the first group. Each channel may be associated with a different filter in a filter bank. The controller may include a processor and/or other electronic components.

In accordance with yet another aspect of the invention, a computer program product for use on a computer system is presented for stimulating electrodes in a multichannel electrode array, each channel associated with an electrode in the array. The computer program product includes a computer usable medium having computer readable program code thereon. The computer readable program code includes program code for defining at least two groups of channels in the multichannel array such that at least one of the defined groups includes a plurality of channels; program code for selecting one or more channels in each group; program code for activating the electrodes associated with each selected channel; and program code for repeating selecting at least one channel in each selected group, and activating the electrodes associated with each selected channel, such that the selected channels in at least one selected group varies.

In accordance with related embodiments of the invention, the program code for activating the electrodes may sequentially activate the electrodes associated with each selected channel. Alternatively, the program code for activating the electrodes may simultaneously activate the electrodes of each selected channel. The program code for activating the electrodes may further include program code for applying compensation for channel interaction. The multichannel electrode array may be part of a cochlear implant for simulating the acoustic nerve. The program code for defining at least two groups of channels in the multichannel array may include program code for defining a first group of channels that includes neighboring electrodes, wherein, due to spatial channel interaction, activating one of the neighboring electrodes in the first group provides stimulation to those regions of the acoustic nerve associated with all of the neighboring electrodes in the first group.

BRIEF DESCRIPTION OF THE DRAWINGS

The foregoing features of the invention will be more readily understood by reference to the following detailed description, taken with reference to the accompanying drawings, in which:

FIG. 3 shows exemplary selected groups in a conventional CIS system (Prior Art);

FIG. 4 shows exemplary selected groups based on an N-of-M strategy (Prior Art);

FIG. 5 shows exemplary selected groups providing, without limitation, constant activity in all cochlear regions, in accordance with one embodiment of the invention;

FIG. 6 shows exemplary selected groups that, without limitation, advantageously provides good temporal representation, in accordance with an embodiment of the invention; and FIG. 7 shows exemplary selected groups that include simultaneous stimulation, in accordance with an embodiment of the invention.

DETAILED DESCRIPTION OF SPECIFIC EMBODIMENTS

In illustrative embodiments, a novel system and method for activating electrodes in an implanted electrode array is presented. The system is capable of increased stimulation rates compared to "continuous-interleaved-sampling strategies" (CIS), while preventing, for example, "micro-shocks" encountered in an N-of-M strategy. Details are discussed below.

Figure 1:
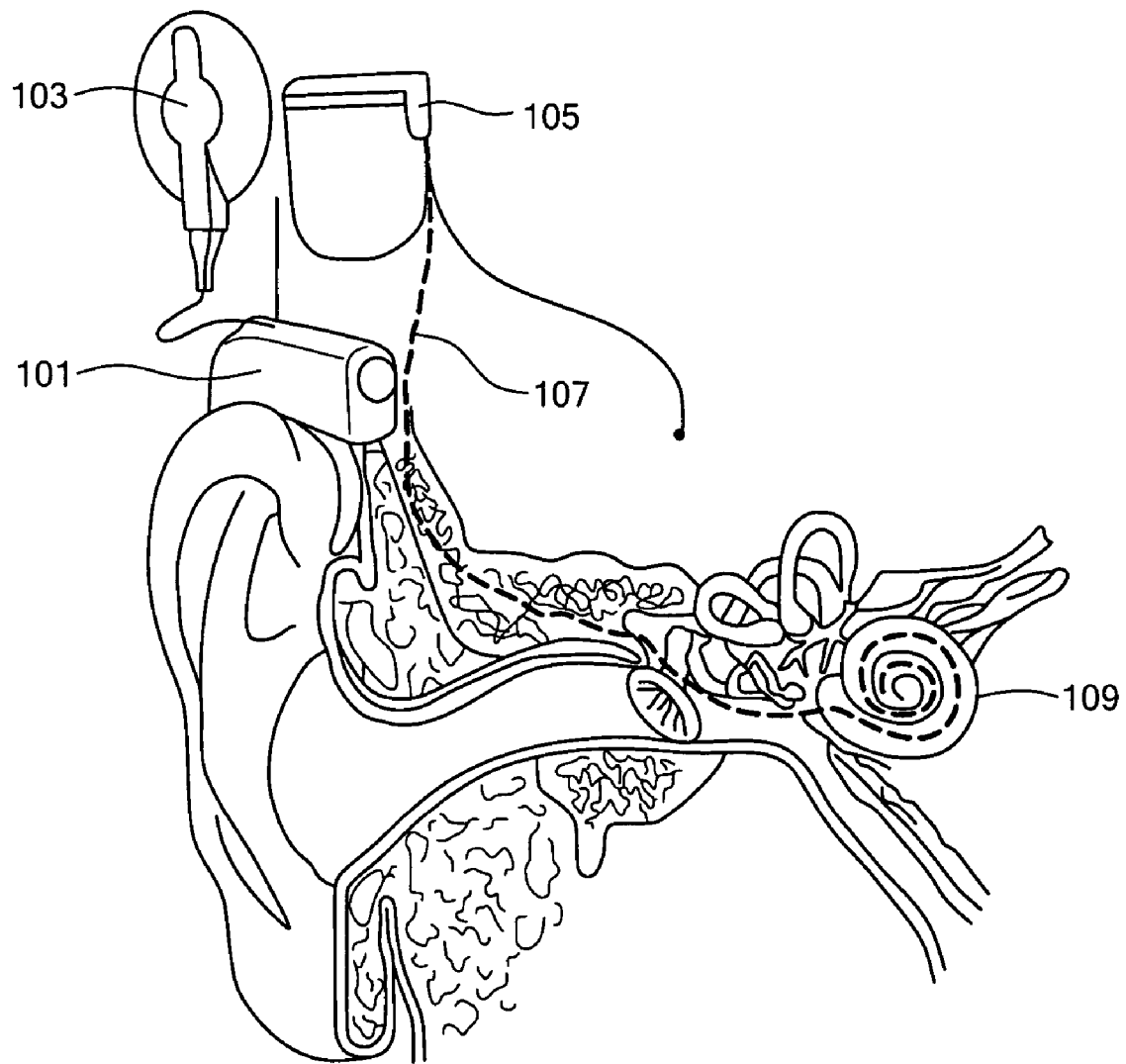
FIG. 1 is a graphical illustration of a cochlear prosthesis (PRIOR ART)
Figure 2:
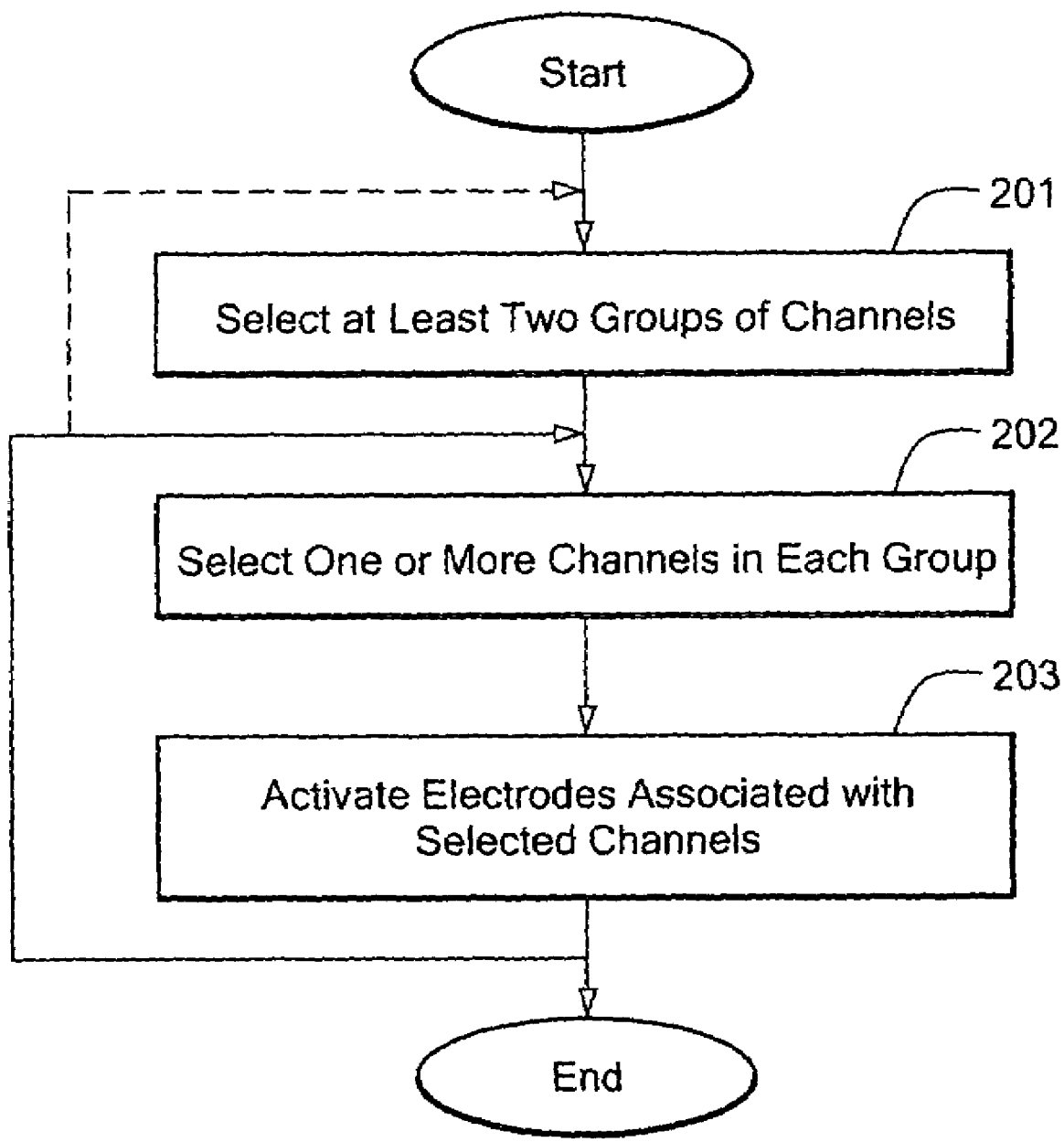
FIG. 2 is a flow chart illustrating a method for activating electrodes in a multichannel electrode array, in accordance with an embodiment of the invention.

FIG. 2 is a flow chart illustrating a method of activating electrodes in a multichannel electrode array, in accordance with an embodiment of the invention. The multichannel electrode array 107 may be part of, without limitation, a cochlear implant having two parts; the speech processor 101 and the implanted stimulator 105 (see FIG. 1). The electrodes may be arranged in a monopolar configuration in which a remote ground electrode is used, or in a bipolar configuration wherein each active electrode has a corresponding reference electrode. The method may be implemented, at least in part, by a controller integrated into the speech processor 101 and/or stimulator 105. The controller may include, without limitation, a circuit and/or a processor that may be pre-programmed or configured to be loaded with an appropriate program.

Each channel in the multichannel electrode array 107 is typically, although not necessarily, associated with a different electrode in the array 107, and may be further associated with a band pass filter, envelope detector, and/or a compressor. The band pass filter may be part of a filter bank located in the speech processor 101, which splits a received audio signal into spectral bands. The output of the band pass filter may undergo further signal processing, such as envelope detection and compression. The amplitudes of the stimulation pulses, provided by the implanted stimulator 105 and used to active the channel's associated electrode, are typically a function of the compressed envelope of the channel's filter output signal. Typically, the basic stimulation waveform is, without limitation, a symmetrical, biphasic pulse.

Referring back to FIG. 2, in illustrative embodiments of the invention at least two groups of channels are selected (hereinafter "selected groups"), wherein at least one selected group has a plurality of channels, step 201. The selected groups may be predefined, and stored for example, in a memory device. The memory device may be, for example, a diskette, a fixed disk, a Compact Disk (CD), Read Only Memory (ROM), Erasable Programmable Read-Only Memory (EPROM), and/or Random Access Memory (RAM). As described in more detail in Example 3 below, the selected groups may be selected such that the spatial channel interaction between the channels in a selected group ensures constant activity in all cochlear areas.

The method then continues to step 202, in which at least one channel within each group is selected. Selecting the at least one channel in the group may be a function of any suitable criteria. For example, the selection may be based on the filter output amplitudes associated with the given channels in the group. In various embodiments, the channels in the groups that have the maximum amplitude may be selected.

The electrodes of the selected channels are then activated in step 203. The electrodes of the selected channels may be activated sequentially or simultaneously. In the latter case, numerical methods of "channel interaction compensation," may be used, as known in the art and described in Zierhofer C M, "Electrical nerve stimulation based on channel specific sampling sequences," U.S. patent application Ser. No. 09/648, 687, filed July 2002, which issued as U.S. Pat. No. 6,594,525 on Jul. 15, 2003, and which is incorporated herein, in its entirety, by reference.

The steps of selecting at least one channel in each selected group and activating the electrodes associated with each selected channel are repeated, such that that the selected channels in at least one selected group varies. In various embodiments, the selected groups may also vary between stimulation cycles based on any suitable criteria (illustrated by the dotted line in FIG. 2).

The following examples are now provided assuming, without limitation, a 12-channel system with sequential and/or parallel stimulation, where the electrode addresses are within the range [1-12]. For all examples, pulses with equal phase durations and a maximum pulse repetition rate R is assumed. Selected groups are represented within brackets, and the index after the closing bracket represents the number of selected maximum channels a within the group, and whether the selected channels are activated sequentially "s" or in parallel "p" (i.e., simultaneously). The first two examples are special cases representing conventional CIS- and conventional N-of-M strategies.

EXAMPLE 1

Prior Art—"Conventional CIS"

In Example 1, selected groups in a conventional CIS system are shown in FIG. 3 (Prior Art). One CIS-stimulation cycle includes 12 selected groups 30. Each selected group 30 is composed of one channel. Since only one channel is present, it is the maximum itself (trivial case). Thus, this setting represents standard 12-channel CIS. The cycle repetition rate is R/12.

EXAMPLE 2

Prior Art—"N-of-M"

In Example 2, one stimulation cycle using an N-of-M strategy contains only one selected group 40, which is composed of all 12 channels, as shown in FIG. 4 (Prior Art). The six channels with maximum energy are selected. Thus, this setting represents a conventional 6-of-12 setting. The cycle repetition rate is R/6, which is an enhancement by a factor of 2 as compared to example 1.

EXAMPLE 3

In Example 3, one stimulation cycle contains six selected groups 50, as shown in FIG. 5 in accordance with an embodiment of the invention. Each selected group comprises two channels, and the channel with the greatest amplitude is selected. The cycle repetition rate is R/6 which is equal to example 2. However, an advantage over the N-of-M (example 2) is that permanent activity in all cochlear regions may be realized, comparable to standard CIS (Example 1). For example, in standard CIS, channels 1 and 2 are updated with a rate R/12, respectively. Assuming a considerable spatial channel interaction between neighboring channels, the "cochlear region" associated to channels 1 and 2 is thus updated on average by a rate of R/6. In Example 3, one of the two channels 1 or 2 is selected, and thus the associated cochlear region is also updated with R/6.

EXAMPLE 4

In Example 4, one stimulation cycle contains ten selected groups 60, as shown in FIG. 6 in accordance with an embodiment of the invention. Group $[12]_{2S}$ appears 5 times in one stimulation cycle, and both amplitudes are selected. The remaining selected groups contain different channels, and one maximum channel is selected. This might reflect a situation, where a good temporal representation is especially important for channels 1 and 2 (e.g., apical channels for representation of temporal fine structure), whereas the remaining channels need less temporal resolution. In this setting, channels 1 and 2 are updated with R/3, respectively, whereas the remaining "cochlear regions" are updated with R/15, respectively.

EXAMPLE 5

In example 5, a stimulation cycle includes three selected groups 70, with the two selected channels in the third group activated simultaneously (i.e., in parallel using simultaneous pulses), as shown in FIG. 7 in accordance with an embodiment of the invention. Applying simultaneous pulses advantageously maximizes data transfer time, saving time compared to a sequential pulse sequence. The amplitudes of the simultaneously activated channels in the third group may take into account parameters of spatial channel interaction, and are not limited to channels that have no or minimal spatial channel interaction. Note that a stimulation cycle may include any combination of simultaneous pulses and/or sequential pulses. In example 5, the selected channels in the first two groups are activated sequentially, with the third group being activated simultaneously.

As described in U.S. Pat. No. 6,594,525, the simultaneous pulses described in Example 5 may be, without limitation, sign-correlated. As described above, spatial channel interaction means that there is considerable geometric overlapping of electrical fields at the location of the excitable nervous tissue, if different stimulation electrodes (positioned in the scala tympani) are activated. Due to conductivity in the scala tympani, simultaneous stimulation of two or more electrodes against a remote ground electrode generally results in a temporal mixture of constructive and destructive superposition of electrical fields at the position of the neurons. For example, if two simultaneous stimulation channels produce currents with equal amplitudes, but different signs, most of the current will flow through the shunt conductance between the two electrodes and will not reach the intended neurons. This additional effect can be removed, if "sign-correlated" pulses are employed. Sign-correlated here means that if two or more pulses occur simultaneously at different electrodes, positive and negative phases are absolutely synchronous in time. This ensures that the sum of the magnitudes of the single stimulation currents is forced to flow into the reference electrode. Thus, at the site of the excitable neurons, only constructive superposition of currents is possible. The stimulation currents in the sign-correlated pulses may be determined, without limitation, such that at least the potentials at the position of the electrodes are equal as in the case of single channel stimulation. In various embodiments, it may be assumed that a single electrode causes exponential decays of the potentials at both sides of the electrode, allowing for a computationally efficient calculation of the pulse amplitudes, since a tri-diagonal matrix is involved.

Alternative embodiments of the invention, may be implemented as, or otherwise include, a computer program product for use with a computer system. Such implementation may include a series of computer instructions fixed either on a tangible medium, such as a computer readable media (e.g., a diskette, CD-ROM, ROM, or fixed disk), or fixed in a computer data signal embodied in a carrier wave that is transmittable to a computer system via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method of activating electrodes in a multichannel electrode array, each channel associated with an electrode in the array, the method comprising:
   selecting at least two groups of channels in the multichannel electrode array, at least one of the selected groups including a plurality of channels;
   selecting one or more channels in each selected group;
   activating the electrodes associated with each selected channel; and repeating selecting at least one channel in each selected group, and activating the electrodes associated with each selected channel, such that the selected channels in at least one selected group varies.

2. The method according to claim 1, wherein activating includes sequentially activating the electrodes associated with each selected channel.

3. The method according to claim 1, wherein activating includes simultaneously activating the electrodes associated with each selected channel.

4. The method according to claim 3, wherein activating includes applying compensation for channel interaction.

5. The method according to claim 1, wherein the multichannel electrode array is part of a cochlear implant, the method further comprising:
   positioning the multichannel electrode array so as to stimulate the acoustic nerve.

6. The method according to claim 5, wherein selecting the at least two groups of channels includes selecting a first group of channels that includes neighboring electrodes, wherein, due to spatial channel interaction, activating one of the neighboring electrodes in the first group provides stimulation to those regions of the acoustic nerve associated with all of the neighboring electrodes in the first group.

7. The method according to claim 1, wherein each channel is associated with a different filter in a filter bank, the method further comprising applying an acoustic representative electrical signal to the bank of filters, wherein activating the electrodes of each selected channel includes performing at least one of envelope detection and nonlinear compression on the selected channel's filter output.

8. The method according to claim 7, wherein selecting one or more channels in each selected group is based, at least in part, on a comparison of the filter outputs associated with the channels in the selected group.

9. A system for stimulating electrodes, the system including:
   a multichannel electrode array, each channel associated with an electrode in the array;
   a controller for defining at least two groups of channels in the multichannel array such that at least one of the defined groups includes a plurality of channels, selecting one or more channels in each group, activating the electrodes associated with each selected channel, and repeating the steps of selecting at least one channel in each selected group, and activating the electrodes associated with each selected channel, such that the selected channels in at least one selected group varies.

10. The system according to claim 9, wherein the controller sequentially activates the electrodes associated with each selected channel.

11. The system according to claim 9, wherein the controller simultaneously activates the electrodes of each selected channel.

12. The system according to claim 11, wherein the controller applies compensation for channel interaction.

13. The system according to claim 9, wherein the multichannel electrode array is part of a cochlear implant for simulating the acoustic nerve.

14. The system according to claim 13, wherein the controller defines a first group of channels that includes neighboring electrodes, wherein, due to spatial channel interaction, activating one of the neighboring electrodes in the first group provides stimulation to those regions of the acoustic nerve associated with all of the neighboring electrodes in the first group.

15. The system according to claim 9, wherein each channel is associated with a different filter in a filter bank.

16. The system according to claim 9, wherein the controller includes a processor.

17. A computer program product for use on a computer system for stimulating electrodes in a multichannel electrode array, each channel associated with an electrode in the array, the computer program product comprising a computer usable medium having computer readable program code thereon, the computer readable program code including:
   program code for defining at least two groups of channels in the multichannel array such that at least one of the defined groups includes a plurality of channels;
   program code for selecting one or more channels in each group;
   program code for activating the electrodes associated with each selected channel; and
   program code for repeating selecting at least one channel in each selected group, and activating the electrodes associated with each selected channel, such that the selected channels in at least one selected group varies.

18. The computer program product according to claim 17, wherein the program code for activating the electrodes sequentially activates the electrodes associated with each selected channel.

19. The computer program product according to claim 17, wherein the program code for activating the electrodes simultaneously activates the electrodes of each selected channel.

20. The computer program product according to claim 19, wherein the program code for activating the electrodes further includes program code for applying compensation for channel interaction.

21. The computer program product according to claim 17, wherein the multichannel electrode array is part of a cochlear implant for simulating the acoustic nerve.

22. The computer program product according to claim 21, wherein the program code for defining at least two groups of channels in the multichannel array include program code for defining a first group of channels that includes neighboring electrodes, wherein, due to spatial channel interaction, activating one of the neighboring electrodes in the first group provides stimulation to those regions of the acoustic nerve associated with all of the neighboring electrodes in the first group.

* * * * *